United States Patent [19]

Wu

[11] 4,371,721

[45] Feb. 1, 1983

[54] SELECTIVE CRACKING OF DISUBSTITUTED BENZENES HAVING POLAR SUBSTITUENTS

[75] Inventor: Margaret May–Som Wu, Belle Mead, N.J.

[73] Assignee: Mobil Oil Corporation, New York, N.Y.

[21] Appl. No.: 305,570

[22] Filed: Sep. 25, 1981

Related U.S. Application Data

[63] Continuation-in-part of Ser. No. 969,745, Dec. 14, 1978, abandoned.

[51] Int. Cl.³ .................. C07C 37/86; C07C 17/38; C07C 45/85; C07C 85/26
[52] U.S. Cl. .................. 568/750; 568/27; 568/28; 568/38; 568/324; 568/576; 568/939; 568/949; 568/751; 564/183; 564/272; 564/424; 562/494; 560/103; 260/453 A; 260/454; 260/465 B; 568/438; 570/190; 570/211
[58] Field of Search .............. 568/750, 751, 438, 426; 570/190, 211; 564/424

[56] References Cited

U.S. PATENT DOCUMENTS

| | | | |
|---|---|---|---|
| 3,856,873 | 12/1974 | Burress | 585/481 |
| 4,163,028 | 7/1979 | Tabak et al. | 585/481 |
| 4,181,811 | 1/1980 | Young | 585/486 |
| 4,197,413 | 4/1980 | Kaeding et al. | 568/798 |
| 4,205,189 | 5/1980 | Young et al. | 568/768 |
| 4,230,894 | 10/1980 | Young | 568/768 |

FOREIGN PATENT DOCUMENTS 432 1/1979 European Pat. Off.
812 2/1979 European Pat. Off.

*Primary Examiner*—Bernard Helfin
*Attorney, Agent, or Firm*—Charles A. Huggett; Ronald J. Cier; George W. Allen

[57] ABSTRACT

A process for selective cracking of 1,4-disubstituted benzene compounds having at least one polar substituent. Mixtures containing isomers of such a compound are brought into contact with a specified type of shape selective crystalline zeolite catalyst under conditions of temperature and pressure conducive to reaction of said benzene compound, thereby selectively reacting the 1,4-disubstituted isomer in preference to the 1,2- and 1,3-disubstituted isomers of said polar benzene compound. The shape selective zeolite catalysts employed herein are crystalline zeolites characterized by a silica to alumina ratio of at least about 12 and a constraint index within the approximate range of 1 to 12.

20 Claims, No Drawings

SELECTIVE CRACKING OF DISUBSTITUTED BENZENES HAVING POLAR SUBSTITUENTS

CROSS REFERENCE TO RELATED APPLICATION

This application is a continuation-in-part of the application of Margaret May-Som Wu having Ser. No. 969,745, filed Dec. 14, 1978, now abandoned.

FIELD OF THE INVENTION

The invention is directed to a process for the removal of polar 1,4-disubstituted benzene compounds, from mixtures containing other isomers of such compounds, by selective cracking in the presence of a particular type of crystalline zeolite catalysts.

BACKGROUND OF THE INVENTION

The time-honored method of isolating or removing particular positional isomers from isomeric mixtures of disubstituted aromatic compounds has been the classical fractional distillation technique. This method, however, has not been very practical on an industrial scale unless there is a significant difference in the boiling points of the various isomers. In terms of many important industrial aromatic compounds, particularly those having one or more polar substituents, separation or significant enrichment of particular isomers by boiling point is an extremely difficult and expensive endeavor, and at times is quite impossible. The table below will illustrate the problem with the boiling points of a few typical compounds.

| Name | B.P., °C. | | |
|---|---|---|---|
| | ortho | meta | para |
| Hydroxy isopropyl benzene (isopropylphenol) (cumenol) | 213-4[a] | 228[a] | 228-30[b] |
| Amino isopropyl benzene (isopropylaniline) | 220-1[b] | | 225[a] |
| Chloro isopropyl benzene (chlorocumene) | 191[c] | 65[7mm] 62-68[8mm] | 198.3[a] |
| Methyl benzaldehyde (tolualdehyde) | 200[a] | 199[a] | 204-5[a] |
| Chlorobenzaldehyde | 211.9[a] | 213-4[a] | 213-4[a] |

[a]760 mm Hg
[b]745 mm Hg
[c]745.6 mm Hg

U.S. Pat. No. 3,029,300 to Schaeffer discloses a selective clathration process for the separation of xylene isomers, but such a process involves an elaborate procedure requiring the employment of very specialized and expensive equipment.

A catalytic process for the selective production of particular xylene isomers, utilizing a platinum on alumina catalyst, is disclosed in U.S. Pat. No. 3,078,318 to Berger.

Selective production of para dialkylbenzenes in the presence of specific zeolite catalysts is described in U.S. Pat. Nos. 3,965,209 to Butter, et al.; 4,001,346 to Chu; 4,086,287 to Kaeding et al; and 4,090,981 to Rodewald.

While the above-noted prior art is considered of interest in connection with the subject matter of the present invention, the selective cracking process described herein utilizing the specified type of zeolitic catalyst to achieve selective removal of 1,4-disubstituted aromatic compounds having polar substituents from mixtures containing the 1,2 and 1,3 isomers of such compounds has not, insofar as is known, been heretofore disclosed.

SUMMARY OF THE INVENTION

It has now been discovered that, by employing a particular type of crystalline zeolite catalyst, one may selectively crack polar 1,4-disubstituted aromatic molecules in preference to the 1,2- and 1,3-isomers of the same aromatic molecules. Isomeric mixtures, such as those resulting from the synthesis of disubstituted aromatics having one or more polar substituents, may thereby be conveniently, efficiently and economically enriched in the 1,2- and/or the 1,3-isomers in good yield using relatively mild conditions. Following the teachings of this invention, polar 1,3-disubstituted and/or 1,2-disubstituted aromatics may be selectively produced either as the sole isomers or as the major isomers in admixture with a minor amount of the polar 1,4-disubstituted compound.

The hereindisclosed process involves contacting an isomeric mixture of disubstituted aromatic compounds, e.g., of a disubstituted benzene compound, containing one or more polar functions, under conditions of temperature and pressure conducive to catalytic cracking, with a specified type of shape selective crystalline zeolite catalyst, whereupon the 1,4-disubstituted isomer is selectively reacted, thereby leaving the product enriched in the 1,2- and/or 1,3-disubstituted isomer. The reaction is conducted at a temperature of between about 150° C. and 600° C., preferably within the approximate range of about 300° C. to 450° C. The zeolitic catalyst found useful herein is characterized by a silica to alumina ratio of at least about 12 and a constraint index, as hereinafter defined, within the approximate range of 1 to 12.

DESCRIPTION OF SPECIFIC EMBODIMENTS

The polar aromatic compounds of interest in the process of this invention comprise those defined by the generic formula:

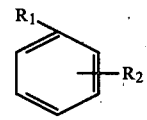

wherein $R_1$ is a polar substituent and $R_2$ is a polar group the same as or different from $R_1$, or a non-polar group such as alkyl, alkenyl or alkynyl. Examples of suitable polar substituents include amino, amido, imino, imido, nitro, nitroso, cyano, cyanato, thio, thiocyano, thiocyanato, acetyl, formyl, carbamyl, carboxy, carboxylate, hydroxy, hydroperoxy, halogen (halo), haloalkyl, sulfinyl and sulfonyl. It is to be understood that any of these polar substituents may themselves be substituted in conventional manner, and these terms are used herein to include such substituted derivatives. Preferred polar substituents include halogen, haloalkyl, hydroxy, amino, nitro, formyl, acetyl and carboxy.

In accordance with the present invention, mixtures comprising positional isomers of one or more such polar disubstituted aromatic compounds, said isomers being the 1,3-isomer and/or the 1,2-isomer with at least some of the 1,4-isomer present, are brought into contact, under cracking conditions, with a particulate catalyst comprising a specific type of crystalline zeolite as hereinafter defined. The 1,4-disubstituted isomer is selectively removed from the mixture relative to the 1,2 and/or 1,3 isomers of the same compound, in its entirety or at least in substantial part, by carrying out the process at temperatures of between about 150° C. and 600° C., pressures of between about $10^4$ N/m$^2$ about $10^6$ N/m$^2$ (0.1 to 10 atmospheres) and a feed weight hourly space velocity (WHSV) of between about 0.1 and about 10. The latter WHSV is based upon the weight of the catalyst compositions, i.e. the total weight of active catalyst and binder therefor. It is preferred that contact between the catalyst and the polar disubstituted aromatic compounds be carried out at from about 300° C. to about 450° C., and a WHSV of from about 1 to 5. Although the reaction normally takes place at atmospheric pressure, the preferred pressure range extends from about $5 \times 10^4$ to about $2 \times 10^5$ N/m$^2$ (0.5 to 2 atmospheres). The 1,3-disubstituted aromatic compounds and/or the 1,2-disubstituted aromatics, singly or together as desired, may be separated from the reaction effluent by any suitable means.

The process of this invention may be carried out as a batch-type, semi-continuous or continuous operation utilizing a fixed, fluidized or moving bed catalyst system. A preferred embodiment entails use of a fluidized catalyst zone wherein the reactants, i.e. the isomeric mixture of disubstituted aromatic compounds, are passed concurrently or countercurrently through a moving fluidized bed of the catalyst. The fluidized catalyst after use is conducted to a regeneration zone wherein coke is burned from the catalyst in an oxygen-containing atmosphere, e.g. air, at an elevated temperature, after which the regenerated catalyst is recycled to the conversion zone for further contact with the aromatic reactants.

The process may be carried out in a system wherein the polar disubstituted compounds are in either the liquid or the vapor state, and the mixture of polar aromatic compounds may be substantially pure (i.e. contain no substantial quantity of hydrocarbon material other than said mixed isomers of said polar disubstituted aromatic material) or may contain substantial amounts of other hydrocarbon material. The latter situation is such as may exist when the feed stream for the instant process also comprises the effluent stream of an earlier upstream process, for instance a process for the manufacture of such disubstituted aromatic compounds. Also, the feed stream for the process of this invention may contain other inert materials as diluents or solvents. Suitable diluents include, but are not limited to: benzene, toluene, xylenes, nitrogen, carbon dioxide, water, carbon monoxide, helium, hydrogen, organic acids (for example formic and acetic acids), etc.

The crystalline zeolite utilized herein are members of a novel class of zeolites that exhibits unusual properties. Although these zeolites have unusually low alumina contents, i.e. high silica to alumina ratios, they are very active even when the silica to alumina ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by controlled burning at higher than usual temperatures to restore activity. These zeolites, used as catalysts, generally have low coke-forming activity and therefore are conducive to long times on stream between regenerations by burning with oxygen-containing gas such as air.

An important characteristic of the crystal structure of this class of zeolites is that it provides constrained access to and egress from the intracrystalline free space by virtue of having an effective pore size intermediate between the small pore Linde A and the large pore Linde X, i.e. the pore windows of the structure have about a size such as would be provided by 10-membered rings of silicon and aluminum atoms interconnected by oxygen atoms. It is to be understood, of course, that these rings are those formed by the regular disposition of the tetrahedra making up the anionic framework of the crystalline zeolite the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the intracrystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intercrystalline sorption capacity for normal hexane which is greater than that for water, i.e. they exhibit "hydrophobic" properties. It is believed that this hydrophobic character is advantageous in the present invention.

The zeolites useful in this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than hexane is excluded and the zeolite is not of the desired type. Windows of 10-membered rings are preferred, although in some instances excessive puckering of the rings or pore blockage may render these zeolites ineffective. Twelve-membered rings usually do not offer sufficient constraint to produce the advantageous conversions, although the puckered 12-ring structure of TMA offretite shows constrained access. Other 12-ring structures may exist which may be operative.

Rather than attempt to judge from crystal structure whether or not a zeolite possesses the necessary constrained access to molecules larger than normal paraffins, a simple determination of the "Constraint Index" as herein defined may be made by passing continuously a mixture of an equal weight of hexane and 3-methylpentane over a small sample, approximately one gram or less, of the zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature adjusted between 290° C. and 510° C. to give an overall conversion between 10% and 60%. The mixture of hydrocarbons is passed at 1 liquid hourly space velocity (i.e. 1 volume of When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space. It is possible that the unusual sustained activity and stability of this class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | | 1.8 |
| ZSM-23 | | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above described crystalline zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix on an anhydrous basis may vary widely with the zeolite content ranging from between about 1 to about 99 percent by weight and more usually in the range of about 5 to about 80 percent by weight of the dry composite.

The crystalline zeolites employed may be modified prior to use by combining therewith a small amount, generally in the range of about 0.5 to about 40 weight percent, preferably of a difficultly reducible oxide, such as the oxides of phosphorous or magnesium or combinations thereof. Modification of the zeolite with the desired oxide or oxides can readily be effected by contacting the zeolite with a solution of an appropriate compound of the element to be introduced, followed by drying and calcining to convert the compound to its oxide form.

Representative phosphorus-containing compounds which may be used include derivatives of groups represented by $PX_3$, $RPX_2$, $R_2PX$, $R_3P$, $X_3PO$, $(XO_3)PO$, $(XO)_3P$, $R_3P=O$, $R_3P=S$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as a phenyl radical and X is hydrogen, R, or halide. These compounds include primary, $RPH_2$, secondary, $R_2PH$ and tertiary, $R_3P$, phosphines such as butyl phosphine; the tertiary phosphine oxides $R_3PO$, such as tributylphosphine oxide, the tertiary phosphine sulfides, $R_3PS$, the primary, $RP(O)(OX)_2$, and secondary, $R_2P(O)OX$, phosphonic acids such as benzene phosphonic acid; the corresponding sulfur derivatives such as $RP(S)(SX)_2$ and $R_2P(S)SX$, the esters of the phosphonic acids such as diethyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiry; $(RO)_3P$, phosphites; and esters thereof such as the monopropyl ester, alkyl dialkylphosphinites, $(RO)PR_2$, and dialkyl alkylphosphonite, $(RO)_2PR$ esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite; and pyrophosphites such as tetraethylpyrophosphite. The alkyl groups in the mentioned compounds contain one to four carbon atoms.

Other suitable phosphorus-containing compounds include the phosphorus halides such as phosphorus trichloride, bromide, and iodide, alkyl phosphoroditchloridites, $(RO)PCl_2$, dialkyl phosphorochloridites, $(RO)_2PX$, dialkylphosphionochloridites, $R_2PCl$, alkyl alkylphosphonochloridates, $(RO)(R)P(O)Cl$, dialkylphosphinochloridates, $R_2P(O)Cl$ and $RP(O)Cl_2$. Appliliquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromotography, to determine the fraction remaining unchanged for each of the two hydrocarbons.

The "Constraint Index" is calculated as follows:

$$\text{Constraint Index} = \frac{\log^{10}(\text{fraction of hexane remaining})}{\log^{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical zeolites are:

| Zeolite | C.I. |
| --- | --- |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Beta | 0.6 |
| ZSM-4 | 0.5 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby have different Constraint Indices. Constraint Index seems to vary somewhat with severity of operation (conversion) and the presence or absence of binders. Therefore, it will be appreciated that it may be possible to so select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the novel class of highly siliceous zeolites are those zeolites which, when tested under two or more sets of conditions within the above specified ranges of temperature and conversion, produce a value of the Constraint Index slightly less than 1, e.g. 0.9, or somewhat greater than 12, e.g. 14 or 15, with at least one other value of 1 to 12. Thus, it should be understood that the Constraint Index value as used herein is an inclusive rather than an exclusive value. That is, a zeolite when tested by any combination of conditions within the testing definition set forth hereinabove to have a Constraint Index of 1 to 12 is intended to be included in the instant catalyst definition regardless that the same identical zeolite tested under other defined conditions may give a Constraint Index value outside of 1 to 12.

The class of zeolites defined herein is exemplified by ZSM-5, ZSM-11, ZSM-12, ZSM-23, ZSM-35, ZSM-38, ZSM-48 and other similar materials. U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-23 is more particularly described in U.S. Pat. No. 4,076,842, the entire content of which is incorporated herein by reference.

ZSM-35 is more particularly described in U.S. Pat. No. 4,016,245, the entire content of which is incorporated herein by reference.

ZSM-38 is more particularly described in U.S. Pat. No. 4,046,859, the entire content of which is incorporated herein by reference.

ZSM-48 is more particularly described in published European Patent Application No. 80 300,463, the entire content of which is incorporated herein by reference.

The specific zeolites described, when prepared in the presence of organic cations, are substantially catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline zeolites include are ZSM-5, ZSM-11, ZSM-12, ZSM-23, ZSM-35, ZSM-38, and ZSM-48, with ZSM-5 ZSM-11 and ZSM-23 being particularly preferred.

In a preferred aspect of this invention, the zeolites hereof are selected as those having a crystal framework density, in the dry hydrogen form, of not less than about 1.6 grams per cubic centimeter. It has been found that zeolites which satisfy all three of these criteria are most desired for several reasons. When hydrocarbon products or by-products are catalytically formed, for example, such zeolites tend to maximize the production of gasoline boiling range hydrocarbon products. Therefore, the preferred zeolites of this invention are those having a Constraint Index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g. on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968.

cable corresponding sulfur derivatives include (RS)PCl$_2$, (RS)$_2$PX, (RS)(R)P(S)Cl and R$_2$P(S)Cl.

Preferred phosphorus-containing compounds include diphenyl phosphine chloride, trimethylphosphite and phosphorus trichloride, phosphoric acid, phenyl phosphine oxychloride, trimethylphosphate, diphenyl phosphinous acid, diphenyl phosphinic acid, diethylchorothiophosphate, methyl acid phosphate and other alcohol-P$_2$O$_5$ reaction products.

Reaction of the zeolite with the phosphorus compound is effected by contacting the zeolite with such compound. Where the treating phosphorus compound is a liquid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the phosphorus-containing compound is, for example, trimethylphosphite or liquid phosphorus trichloride, a hydrocarbon solvent such as octane may be employed. The phosphorus-containing compound may be used without a solvent, i.e., may be used as a neat liquid. Where the phosphorus-containing compound is in the gaseous phase, such as where gaseous phosphorus trichloride is employed, the treating compound can be used by itself or can be used in admixture with a gaseous diluent relatively inert to the phosphorus-containing compound and the zeolite, such as air or nitrogen, or with an organic solvent, such as octane or toluene.

Prior to reacting the zeolite with the phosphorus-containing compound, the zeolite may be dried. Drying can be effected in the presence of air. Elevated temperatures may be employed. However, the temperature should not be such that the crystal structure of the zeolite is destroyed.

Heating of the phosphorus-containing catalyst subsequent to preparation and prior to use is also preferred. The heating can be carried out in the presence of oxygen, for example, air. Heating can be at a temperature of about 150° C. However, higher temperatures, e.g., up to about 500° C., are preferred. Heating is generally carried out for 3–5 hours but may be extended to 24 hours or longer. While heating temperatures above about 500° C. can be employed, they are generally not necessary. At temperatures of about 1000° C. the crystal structure of the zeolite tends to deteriorate.

The amount of phosphorus incorporated with the zeolite should be at least about 0.25 percent by weight. However, it is preferred that the amount of phosphorus in the zeolite be at least about 1 percent by weight when the same is combined with a binder, e.g. 35 weight percent of alumina. The amount of phosphorus can be as high as about 25 percent by weight or more depending on the amount and type of binder present. Preferably, the amount of phosphorus added to the zeolite is between about 0.5 and about 15 percent by weight.

The amount of phosphorus incorporated with the zeolite by reaction with elemental phosphorus or phosphorus-containing compound will depend upon several factors. One of these is the reaction time, i.e., the time that the zeolite and the phosphorus-containing source are maintained in contact with each other. With greater reaction times, all other factors being equal, a greater amount of phosphorus is incorporated with the zeolite. Other factors upon which the amount of phosphorus incorporated with the zeolite is dependent include reaction temperature, concentration of the treating compound in the reaction mixture, the degree to which the zeolite has been dried prior to reaction with the phosphorus-containing compound, the conditions of drying of the zeolite after reaction of the zeolite with the treating compound, and the amount and type of binder incorporated with the zeolite.

Another suitable modifying oxide is that of magnesium. Representative magnesium-containing compound include magnesium acetate, magnesium nitrate, magnesium benzoate, magnesium propionate, magnesium 2-ethylhexoate, magnesium carbonate, magnesium formate, magnesium oxylate, magnesium amide, magnesium bromide, magnesium hydride, magnesium lactate, magnesium laurate, magnesium oleate, magnesium palmitate, magnesium salicylate, magnesium stearate and magnesium sulfide.

Reaction of the zeolite with the treating magnesium compound is effected by contacting the zeolite with such compound. Where the treating compound is a liquid, such compound can be in solution in a solvent at the time contact with the zeolite is effected. Any solvent relatively inert with respect to the treating magnesium compound and the zeolite may be employed. Suitable solvents include water and aliphatic, aromatic or alcoholic liquid. The treating compound may also be used without a solvent, i.e. may be used as a neat liquid. Where the treating compound is in the gaseous phase, it can be used by itself or can be used in admixture with a gaseous diluent relatively inert to the treating compound and the zeolite such as helium or nitrogen, or with an organic solvent such as octane or toluene.

Heating of the magnesium compound impregnated catalyst subsequent to preparation and prior to use is preferred. The heating can be carried out in the presence of oxygen, for example, air. Heating can be at a temperature of about 150° C. However, higher temperatures, e.g. up to about 500° C., are preferred. Heating is generally carried out for 1–5 hours but may be extended to 24 hours or longer. While heating temperatures above about 500° C. may be employed, they are generally not necessary. At temperatures of about 1000° C. the crystal structure of the zeolite tends to deteriorate. After heating in air at elevated temperatures, the oxide form of magnesium is present.

The amount of magnesium oxide incorporated in the zeolite should be at least about 0.25 percent by weight. However, it is preferred that the amount of magnesium oxide in the zeolite be at least about 1 percent by weight, particularly when the same is combined with a binder, e.g. 35 weight percent of alumina. The amount of magnesium oxide can be as high as about 25 percent by weight or more depending on the amount and type of binder present. Preferably, the amount of magnesium oxide added to the zeolite is between about 0.5 and about 15 percent by weight.

In some instances, it may be desirable to modify the crystalline zeolite by combining therewith the oxides of both phosphorus and magnesium. When such modification technique is employed, the oxides may be deposited on the zeolite either sequentially or from a solution containing suitable compounds of both of the elements, the oxides of which are to be combined with the zeolite. The amounts of oxides present in such instance are in the same range as specified above for the individual oxides, with the overall added oxide content being between 0.5 and about 40 weight percent.

In addition to treatment of the zeolite composites with phosphorus and/or magnesium as hereinbefore described in detail, such zeolites may also be treated with a variety of other oxide materials. Such oxide materials include oxides of boron (U.S. Pat. No. 4,067,920); antimony (U.S. Pat. No. 3,979,472); beryllium (U.S. Ser. No. 124,158, filed Feb. 25, 1980); Group VIIA metals (U.S. Ser. No. 124,408, filed Feb. 25, 1980); alkaline earth metals (U.S. Ser. No. 128,688, filed Mar. 10, 1980); Group IB metals (U.S. Ser. No. 153,364, filed May 27, 1980); Group IVB metals (U.S. Ser. No. 137,881, filed Apr. 7, 1980); Group VIA metals (U.S. Ser. No. 130,953, filed Mar. 17, 1980); Group IA elements (U.S. Ser. No. 146,951, filed May 5, 1980); cadmium (U.S. Ser. No. 139,611, filed Apr. 11, 1980); iron and/or cobalt (U.S. Ser. No. 150,868, filed May 19, 1980); Group IIIB metals (U.S. Ser. No. 152,939, filed May 23, 1980); Group IVA metals (U.S. Ser. No. 301,683, filed Oct. 29, 1980); Group VA metals (U.S. Ser. No. 201,899, filed Oct. 29, 1980); and Group IIIA elements (U.S. Ser. No. 212,067, filed Dec. 2, 1980).

Still another modifying treatment entails steaming of the zeolite by contact with an atmosphere containing from about 5 to 100 percent steam at a temperature of from about 250° to about 1000° C. for a period of between about 0.25 and about 100 hours and under pressures ranging from sub-atmospheric to several hundred atmospheres to reduce the alpha value thereof to less than 500, and preferably less than 20, but greater than zero.

Another modifying treatment involves precoking of the catalyst to deposit a coating of between about 2 and about 75, and preferably between about 15 and about 75, weight percent of coke thereon. Precoking can be accomplished by contacting the catalyst with a hydrocarbon charge, e.g. toluene, under high severity conditions or alternatively at a reduced hydrogen to hydrocarbon concentration, e.g. 0 to 1 mole ratio of hydrogen to hydrocarbon, for a sufficient time to deposit the desired amount of coke thereon.

It is also contemplated that a combination of steaming and precoking of the catalyst under the above conditions may be employed to suitably modify the crystalline zeolite catalyst.

The following examples are provided herein to illustrate the process of this invention without intending to set undue limitations thereon.

EXAMPLE 1

A mixture comprising 68.2 mole % 1-hydroxy-3-isopropylbenzene and 31.5 mole % 1-hydroxy-4-isopropylbenzene was passed through a bed comprising 4 grams of HZSM-5 zeolite catalyst at a feed WHSV of 1.2. The pressure was maintained at $10^5$ N/m$^2$ (1 atm) and the temperature varied from 300° C. to 400° C. The results are shown in Table 1.

TABLE 1

| Catalyst: HZSM-5 | | | | |
|---|---|---|---|---|
| | Feedstock | | | |
| Temp. °C. | — | 300 | 350 | 400 |
| WHSV | — | 1.2 | 1.2 | 1.2 |
| Liquid product composition - mole %: | | | | |
| Light ends | 0 | 2.7 | 3.8 | 5.8 |
| Hydroxybenzene | 0 | 24.9 | 38.7 | 53.3 |
| Methylhydroxybenzene | 0 | 0.5 | 0.9 | 1.8 |
| Ethylhydroxybenzene | 0 | 0.05 | 0.3 | 3.2 |
| 1-Hydroxy-2-isopropylbenzene | 0 | 1.4 | 1.3 | 0 |
| 1-Hydroxy-3-isopropylbenzene | 68.2 | 60.3 | 48.2 | 28.8 |
| 1-Hydroxy-4-isopropylbenzene | 31.5 | 9.7 | 4.5 | 2.3 |
| Other | 0 | 0.4 | 2.3 | 4.7 |

TABLE 1-continued

| Catalyst: HZSM-5 | | | | |
|---|---|---|---|---|
| | Feedstock | | | |
| % Hydroxyisopropylbenzene: | | | | |
| 1,2-isomer | 0 | 2.0 | 2.4 | 0 |
| 1,3-isomer | 68.2 | 84.4 | 89.2 | 92.6 |
| 1,4-isomer | 31.5 | 13.6 | 8.4 | 7.4 |
| Conversion, mole %: | | | | |
| 1,3-isomer | — | 11.6 | 29.3 | 57.8 |
| 1,4-isomer | — | 69.2 | 85.7 | 92.6 |

As will be seen from the Table, particularly from the entries entitled "Conversion", the 1-hydroxy-4-isopropylbenzene was reacted in a substantially higher amount than was the 1-hydroxy-3-isopropylbenzene, thereby demonstrating the selective character of the process utilizing HZSM-5 zeolite catalyst with a mixed isomer feed stream of disubstituted aromatic compounds containing one polar and one non-polar substituent on the benzene ring. The major product formed was hydroxybenzene, indicating that the mechanism seems to be predominantly dealkylation.

EXAMPLE 2

The same hydroxyisopropylbenzene mixture of Example 1 was passed through 4 grams of calcined amorphous aluminosilicate cracking catalyst (SiO$_2$/Al$_2$O$_3$ ratio 9/1, surface area 450 m$^2$/g) for purposes of comparison with Example 1. The WHSV and pressure were the same as those of Example 1 and the reaction was studied at 300° C. and 350° C. The results were summarized in TABLE 2.

TABLE 2

| Cracking of Hydroxyisopropylbenzene Catalyst: Amorphous aluminosilicate | | | |
|---|---|---|---|
| | Feedstock | | |
| Temp., °C. | — | 300 | 350 |
| WHSV | — | 1.2 | 1.2 |
| Product composition area %: | | | |
| Hydroxybenzene | 0 | 27.8 | 46.8 |
| 1-Hydroxy-2-isopropylbenzene | 0 | 7.1 | 9.2 |
| 1-Hydroxy-3-isopropylbenzene | 68.2 | 41.1 | 22.8 |
| 1-Hydroxy-4-isopropylbenzene | 31.5 | 12.2 | 7.8 |
| Others* | 0.3 | 11.7 | 13.4 |
| % Hydroxyisopropylbenzene: | | | |
| 1,2-isomer | 0 | 11.8 | 23.2 |
| 1,3-isomer | 68.2 | 68.0 | 57.2 |
| 1,4-isomer | 31.5 | 20.2 | 19.6 |
| % Conversion: | | | |
| 1,3-isomer | — | 39.7 | 66.6 |
| 1,4-isomer | — | 61.3 | 75.2 |

*including light gas, hydroxymethylbenzenes, ethylhydroxybenzenes, and t-butylhydroxybenzene.

It is seen that, using a conventional amorphous aluminosilicate catalyst, there has been no enrichment of the 1,3-isomer in the product stream in preference to the 1,4-isomer. In addition, transalkylation and rearrangement would seem to be enhanced in view of the higher yield of the 1,2-isomer.

A composition of Examples 1 and 2 will clearly illustrate the superiority of the present invention over a similar process employing a conventional cracking catalyst.

EXAMPLE 3

ZSM-5 zeolite catalyst was modified by impregnation with magnesium as follows:

NH$_4$.ZSM-5 was pelletized and the pellets crushed and sieved. Five grams of particles in the 14–20 mesh range were soaked in an aqueous solution of magnesium acetate (10 gm.Mg(OAc)$_2$.4H$_2$O in 20 ml. distilled H$_2$O) for 16 hours at room temperature. The catalyst was then filtered, washed with a minimum amount of water and air dried. The catalyst was calcined at 500° C. for 16 hours before use. Subsequent analysis showed the catalyst to contain 3.33 wt.% magnesium as MgO.

EXAMPLE 4

A hydroxyisopropylbenzene mixture comprising 70.0% of the 1,3-isomer and 30.0% of the 1,4-isomer, was brought into contact with 4 grams of the Mg.HZSM-5 catalyst of Example 3. Two runs were made, the first at a feed WHSV of 4 and temperature of 350° C. and the second at feed WHSV of 1.2 and temperature of 440° C. The pressure was maintained at 10$^5$ N/m$_2$ (1 atm) in both runs. The results are summarized in Table 3.

TABLE 3

Selective Cracking of Hydroxyisopropylbenzenes
Catalyst: Mg.HZSM-5

|  | Feedstock |  |  |
|---|---|---|---|
| Temp., °C. | — | 350 | 440 |
| WHSV | — | 4 | 1.2 |
| Product Composition - area %: |  |  |  |
| Hydroxybenzene | 0 | 10.7 | 18.8 |
| 1-Hydroxy-2-isopropylbenzene | 0 | 0 | 0 |
| 1-Hydroxy-3-isopropylbenzene | 67.6 | 67.0 | 65.3 |
| 1-Hydroxy-4-isopropylbenzene | 28.9 | 19.9 | 11.6 |
| Others* | 3.5 | 2.4 | 4.3 |
| % Hydroxyisopropylbenzene: |  |  |  |
| 1,2-isomer | 0 | 0 | 0 |
| 1,3-isomer | 70.0 | 77.1 | 84.8 |
| 1,4-isomer | 30.0 | 22.9 | 15.1 |
| % Conversion |  |  |  |
| 1,3-isomer | — | 0.7 | 3.4 |
| 1,4-isomer | — | 31.2 | 59.8 |

*including light gas, hydroxymethylbenzenes, ethylhydroxybenzenes, and t-butylhydroxybenzenes.

The 1,4-isomer has been selectively reacted and thereby removed from the feed stream with substantially higher efficiency than the 1,3-isomer of the hydroxyisopropylbenzene, again demonstrating the efficacy of the invention. Upon the comparison of the results of this example with those of Example 1 it can be seen that the selectivity of the catalyst for cracking the 1,4-isomer has been improved by modification thereof with magnesium. In like manner it can be shown that addition of phosphous to the catalyst will achieve similar beneficial result.

EXAMPLE 5

A mixture comprising 4.8% of 2-methylbenzaldehyde, 62.4% of 3-methylbenzaldehyde and 31.2% of 4-methylbenzaldehyde was passed over 4 grams of HZSM-5 zeolite catalyst at 350° C. The feed WHSV was 1 and the pressure was 10$^5$ N/m$^2$ (1 atm). The run is summarized in Table 4 below.

TABLE 4

Selective Cracking of Methylbenzaldehydes
Catalyst: HZSM-5

|  | Feedstock |  |
|---|---|---|
| Temp. °C. | — | 350 |
| WHSV | — | 1 |
| Liquid Product Composition - area % |  |  |
| Methylbenzene | 0 | 28.5 |
| 2-Methylbenzaldehyde | 4.8 | 4.2 |
| 3-Methylbenzaldehyde | 62.4 | 60.4 |
| 4-Methylbenzaldehyde | 31.2 | 0.9 |
| Others* | 1.7 | 6.0 |
| % Methylbenzaldehydes: |  |  |
| 2-Methyl isomer | 4.8 | 6.4 |
| 3-Methyl isomer | 63.4 | 92.1 |
| 4-Methyl isomer | 31.7 | 7.8 |
| % Conversion: |  |  |
| 2-Methyl isomer | — | 11.3 |
| 3-Methyl isomer | — | 3.1 |
| 4-Methyl isomer | — | 97.0 |

*includes light gas, benzene and dimethylbenzenes

It is shown that the 4-methylbenzaldehyde has been selectively cracked in preference to both the 2-methylbenzaldehyde and the 3-methylbenzaldehyde. The major product being methylbenzene, it would appear that the reaction mechanism involved is primarily one of selective decarboxylation.

EXAMPLE 6

A similar mixture of methylbenzaldehydes to that used in Example 5 was passed thru the amorphous aluminosilicate cracking catalyst of Example 2 under the same conditions of temperature, pressure and feed rate. The results are summarized in Table 5.

TABLE 5

Cracking of Methylbenzaldehydes
Catalyst: Amorphous aluminosilicate

|  | Feedstock |  |
|---|---|---|
| Temp., °C. | — | 350 |
| WHSV | — | 1 |
| Liquid product composition - area %: |  |  |
| Methylbenzene | 0 | 6.3 |
| 2-Methylbenzaldehyde | 4.1 | 3.6 |
| 3-Methylbenzaldehyde | 64.4 | 56.8 |
| 4-Methylbenzaldehyde | 31.1 | 26.0 |
| Others* | 0.4 | 7.3 |
| % Methylbenzaldehydes: |  |  |
| 2-Methyl isomer | 4.1 | 4.2 |
| 3-Methyl isomer | 64.7 | 65.7 |
| 4-Methyl isomer | 31.2 | 30.1 |
| % Conversion: |  |  |
| 2-Methyl isomer | — | 11.3 |
| 3-Methyl isomer | — | 11.9 |
| 4-Methyl isomer | — | 16.3 |

*includes light gas, benzene and dimethylbenzenes

Using a conventional hydrocarbon cracking catalyst, no significant selectivity for preferential cracking of any isomer was observed.

EXAMPLE 7

An isomeric mixture of chloroisopropylbenzenes, comprising 39.9% 1-chloro-2-isopropylbenzene, 7.1% 1-chloro-3-isopropylbenzene, and 60.0% 1-chloro-4-isopropylbenzene was passed thru 4 grams of HZSM-5 zeolite catalyst at 300° C., feed WHSV of 1.8 and pressure of 10$^5$ N/m$^2$ (1 atm). TABLE 6 below is a summary of the run.

TABLE 6

Selective Cracking of Chloroisopropylbenzenes
Catalyst: HZSM-5

|  | Feedstock |  |
|---|---|---|
| Temp., °C. | — | 300 |
| WHSV | — | 1.8 |

TABLE 6-continued

Selective Cracking of Chloroisopropylbenzenes
Catalyst: HZSM-5

|  |  | Feedstock |
|---|---|---|
| Product composition - area %: |  |  |
| Chlorobenzene | 0 | 31.0 |
| Isopropylbenzene | 0 | 0 |
| 1-Chloro-2-isopropylbenzene | 39.9 | 41.8 |
| 1-Chloro-3-isopropylbenzene | 7.1 | 7.5 |
| 1-Chloro-4-isopropylbenzene | 60.0 | 0 |
| Others* | 0 | 19.6 |
| % Chloroisopropylbenzenes: |  |  |
| 1,2-isomer | 39.9 | 84.7 |
| 1,3-isomer | 7.1 | 15.3 |
| 1,4-isomer | 60.0 | 0 |
| % Conversion: |  |  |
| 1,2-isomer | — | (−4.8) |
| 1,3-isomer | — | (−5.9) |
| 1,4-isomer | — | 100 |

*includes benzene, methylbenzene, ethylbenzene, dimethylbenzenes, chloromethylbenzenes, chloroethylbenzenes, and $C_{10+}$ aromatic compounds.

The 1,4-isomer has been completely reacted, the major product being dealkylation to chlorobenzene. Some transalkylation may have taken place as indicated by the small net increase in the amount of the 1,2- and 1,3-isomer present in the product stream as compared to the feedstream.

EXAMPLE 8

A feedstream comprising 55.3% 1-amino-2-isopropylbenzene and 30.7% 1-amino-4-isopropylbenzene was contacted with 4 grams of HZSM-5 zeolite catalyst at 350° C. The feed WHSV was 1 and the pressure was $10^5$ N/m$^2$ (1 atm). The results are summarized in TABLE 7 below.

TABLE 7

Selective Cracking of Aminoisopropylbenzenes
Catalyst: HZSM-5

|  |  | Feedstock |
|---|---|---|
| Temp., °C. | — | 350 |
| WHSV | — | 1 |
| Liquid product composition - area %: |  |  |
| Aminobenzene | 1.2 | 12.8 |
| 1-Amino-2-isopropylbenzene | 60.3 | 58.1 |
| 1-Amino-4-isopropylbenzene | 30.7 | 22.0 |
| Others* | 7.8 | 7.1 |
| Gaseous product composition - area %: |  |  |
| Air | — | 15.5 |
| $C_3H_6$ | — | 77.9 |
| Other hydrocarbon gases | — | 6.6 |
| % Conversion: |  |  |
| 1,2-isomer | — | 3.7 |
| 1,4-isomer | — | 28.5 |

*includes unidentified aromatic compounds

The 1-amino-4-isopropylbenzene has been selectively reacted in significant preference to the 1-amino-2-isopropyl isomer, the primary products being aminobenzene and propylene.

EXAMPLE 9

The ammonium form of ZSM-11 zeolite catalyst was pelletized, crushed and sieved to 14/20 mesh particles. These were then calcined in air at 500° C. for approximately 3 hours to convert the ammonium form of the catalyst into the hydrogen form. The catalyst was then selectivated by toluene disproportionation at 600° C. for 3 hours to deposit coke thereon.

EXAMPLE 10

A mixture comprising 69.4% 1-hydroxy-3-isopropylbenzene and 30.7% 1-hydroxy-4-isopropylbenzene was passed thru a bed of the HZSM-11 catalyst of Example 9 at 300° C. and $10^5$ N/m$^2$ (1 atm). Two runs were made, one at a feed WHSV of 1.7 and the other at WHSV of 3.2. The results are summarized in TABLE 8 below.

TABLE 8

Selective Cracking of Hydroxy Isopropylbenzenes
Catalyst: HZSM-11

|  |  | Feedstock |  |
|---|---|---|---|
| Temp., °C. | — | 300 | 300 |
| WHSV | — | 1.7 | 3.2 |
| Product composition - area %: |  |  |  |
| Hydroxybenzene | — | 41.9 | 30.9 |
| 1-Hydroxy-2-isopropylbenzene | — | 2.9 | 1.1 |
| 1-Hydroxy-3-isopropylbenzene | 69.4 | 44.0 | 54.6 |
| 1-Hydroxy-4-isopropylbenzene | 30.6 | 4.1 | 3.5 |
| Others | 0 | 7.2 | 9.9 |
| % Hydroxyisopropylbenzenes: |  |  |  |
| 1,2-isomer | 0 | 5.5 | 1.9 |
| 1,3-isomer | 69.4 | 86.5 | 92.2 |
| 1,4-isomer | 30.6 | 8.1 | 5.9 |
| % Conversion: |  |  |  |
| 1,3-isomer | — | 36.7 | 21.3 |
| 1,4-isomer | — | 86.6 | 88.5 |

The HZSM-11 zeolite catalyst shows substantial shape selectivity. The 1,4-isomer of hydroxyisopropylbenzene was converted to hydroxybenzene with significantly higher efficiency than was the 1,3-isomer.

EXAMPLE 11

A similar hydroxyisopropylbenzene feed mixture to that of Example 10 was passed thru a bed comprising 1 gram of the zeolite catalyst HZSM-23. Two runs were made, at 300° C. and 400° C. respectively, both at a feed WHSV of 6.7 and pressure of $10^5$ N/m$^2$ (1 atm). The runs are summarized in TABLE 9.

TABLE 9

Selective Cracking of Hydroxyisopropylbenzenes
Catalyst: HZSM-23

|  |  | Feedstock |  |
|---|---|---|---|
| Temp., °C. | — | 300 | 400 |
| WHSV | — | 6.7 | 6.7 |
| Product composition - area %: |  |  |  |
| Hydroxybenzene | 0 | 2.4 | 21.6 |
| 1-Hydroxy-2-isopropylbenzene | 0 | 0.6 | 2.3 |
| 1-Hydroxy-3-isopropylbenzene | 69.4 | 73.7 | 60.9 |
| 1-Hydroxy-4-isopropylbenzene | 30.6 | 21.8 | 11.7 |
| Others | 0 | 1.5 | 3.6 |
| % Hydroxyisopropylbenzenes: |  |  |  |
| 1,2-isomer | 0 | 0.6 | 2.9 |
| 1,3-isomer | 69.4 | 76.7 | 81.5 |
| 1,4-isomer | 30.6 | 22.7 | 15.6 |
| % Conversion: |  |  |  |
| 1,3-isomer | — | (−6.2) | 12.3 |
| 1,4-isomer | — | 28.8 | 61.9 |

As previously demonstrated for the HZSM-11 zeolite catalysts, the zeolite catalyst designated ZSM-23 is shown to have significant shape selectivity in the preferential cracking of polar disubstituted benzenes.

EXAMPLE 12

A solution comprising 29.3% of 2-chlorobenzaldehyde and 28.5% 4-chlorobenzaldehyde in benzene was passed thru a catalyst bed comprising 4 grams of HZSM-5 catalyst. Runs were carried out at both 300°

C. and 400° C., the feed WHSV and pressure in both cases being maintained at 2.1 and $10^5$ N/m² (1 atm) respectively. The results are summarized in TABLE 10.

TABLE 10
Selective Cracking of Chlorobenzaldehydes
Catalyst: HZSM-5

|  | Feedstock |  |  |
|---|---|---|---|
| Temp., °C. | — | 300 | 400 |
| WHSV | — | 2.1 | 2.1 |
| Product composition - area % |  |  |  |
| Benzene | 41.8 | 42.4 | 42.9 |
| Chlorobenzene | 0 | 23.6 | 28.9 |
| 2-Chlorobenzaldehyde | 29.3 | 23.6 | 23.1 |
| 3-Chlorobenzaldehyde | 0 | 0.04 | 0.1 |
| 4-Chlorobenzaldehyde | 28.5 | 9.2 | 3.9 |
| Others | 0.4 | 1.1 | 1.1 |
| % Chlorobenzaldehyde: |  |  |  |
| 1,2-isomer | 50.6 | 71.9 | 85.4 |
| 1,3-isomer | 0 | 0.1 | 0.2 |
| 1,4-isomer | 49.4 | 28.1 | 14.5 |
| % Conversion |  |  |  |
| 1,2-isomer | — | 19.3 | 21.1 |
| 1,4-isomer | — | 67.6 | 86.2 |

The selectivity of the hereindisclosed selective cracking process is shown to extend to disubstituted benzene compounds wherein both of the substituents are polar groups. In similar manner it can be shown that the described catalysts will selectively crack 1,4-disubstituted aromatics having any two polar substituents, regardless of whether such substituents are the same or different functional moieties.

What is claimed is:

1. A process for selective cracking of a 1,4-disubstituted benzene compound having a polar first substituent selected from hydroxy, formyl, halo and amino and a second substituent selected from halo and alkyl, in an isomeric mixture containing one or more additional isomers of said disubstituted benzene compound, said process comprising contacting said mixture with a crystalline zeolite catalyst at a temperature of between about 300° C. and about 450° C. and a pressure between about $10^4$ N/m² and about $10^6$ N/m², said catalyst being characterized by a silica to alumina ratio of at least 12 and a constraint index within the approximate range of 1 to 12.

2. A process according to claim 1 wherein said isomeric mixture contains both the 1,2 and 1,3 isomer of said polar disubstituted benzene compound in addition to the 1,4 isomer and wherein said process results in a substantial reduction in the amount of said polar 1,4-disubstituted isomer relative to said other isomers.

3. A process according to claim 1 wherein said disubstituted benzene compound has one polar substituent and one substantially non-polar substituent thereon.

4. A process according to claim 1 wherein said disubstituted benzene compounds has two polar substituents thereon.

5. A process according to claim 1 wherein the polar first substituent on said disubstituted benzene compound is selected from hydroxy and halo.

6. A process according to claim 1 wherein said pressure is between about $10^5$ N/m² and about $5 \times 10^5$ N/m².

7. A process according to claim 1 wherein said catalyst has undergone prior modification by combining therewith between about 0.5 and about 40 weight percent of at least one oxide selected from the group consisting of the oxides of phosphorus and magnesium.

8. A process according to claim 1 wherein said catalyst has undergone prior modification by combining therewith between about 1 and 25 weight percent of an oxide of magnesium.

9. A process according to claim 1 wherein said catalyst has undergone prior modification by combining therewith between about 1 and about 25 weight percent of an oxide of phosphorus.

10. A process according to claim 1 wherein said catalyst has undergone prior modification by steaming at a temperature of between about 250° C. and about 1,000° C. for a period of between about 0.5 and about 100 hours.

11. A process according to claim 1 wherein said catalyst has undergone prior modification by the deposition of between about 2 and about 75 weight percent of coke thereon.

12. A process according to claim 1 wherein said catalyst is admixed with a binder therefor.

13. A process according to claim 1 wherein said catalyst is ZSM-5.

14. A process according to claim 13 wherein said ZSM-5 is admixed with a binder therefor.

15. A process according to claim 1 wherein said catalyst is ZSM-11.

16. A process according to claim 15 wherein said ZSM-11 is admixed with a binder therefor.

17. A process according to claim 1 wherein said catalyst is ZSM-23.

18. A process according to claim 17 wherein said ZSM-23 is admixed with a binder therefor.

19. A process according to claim 1 or 2 wherein said polar disubstituted benzene isomers are in admixture with other hydrocarbon compounds.

20. A process according to claim 1, 2, 3, 4, 6, 7, 8, 9, 10, 11, 12, 13, 14, 15, 16, 17 or 18 wherein said disubstituted benzene compound has an alkyl non-polar substituent thereon and a hydroxy polar substituent thereon.

* * * * *